United States Patent
Bigliardi

[11] Patent Number: 5,989,253
[45] Date of Patent: Nov. 23, 1999

[54] LIGAMENT ANCHORING DEVICE

[76] Inventor: Yves Bigliardi, 303 rue des Bosnées, 74460 Marnaz, France

[21] Appl. No.: 09/051,021
[22] PCT Filed: Oct. 25, 1996
[86] PCT No.: PCT/FR96/01672
§ 371 Date: Mar. 30, 1998
§ 102(e) Date: Mar. 30, 1998
[87] PCT Pub. No.: WO97/15244
PCT Pub. Date: May 1, 1997

[30] Foreign Application Priority Data

Oct. 27, 1995 [FR] France .................................. 95/12910

[51] Int. Cl.⁶ .................................................. A61B 17/00
[52] U.S. Cl. .................................................. 606/72
[58] Field of Search ................ 606/72, 73, 74, 606/75, 60, 65, 80, 85, 104, 232, 79, 88; 623/13

[56] References Cited

U.S. PATENT DOCUMENTS

| | | | |
|---|---|---|---|
| Re. 34,871 | 3/1995 | McGuire et al. | 606/73 |
| 4,484,570 | 11/1984 | Sutter et al. | 606/72 |
| 4,950,270 | 8/1990 | Bowman et al. | 606/72 |
| 5,643,266 | 7/1997 | Li | 606/72 |
| 5,643,321 | 7/1997 | McDevitt | 606/232 |
| 5,702,398 | 12/1997 | Thrabishy | 606/72 |

FOREIGN PATENT DOCUMENTS

| | | |
|---|---|---|
| 0596177 | 5/1994 | European Pat. Off. . |
| 0596829 | 5/1994 | European Pat. Off. . |
| 2586927 | 3/1987 | France . |
| 2671717 | 7/1992 | France . |
| 2696925 | 4/1994 | France . |
| 4106823 | 6/1992 | Germany . |
| 9210031 | 9/1992 | Germany . |

Primary Examiner—Michael Buiz
Assistant Examiner—Vikki Trinh
Attorney, Agent, or Firm—William H. Eilberg

[57] ABSTRACT

A device including an elongate body (15) with anti-rotation projections on the peripheral side surface thereof and a generally flat side bearing surface (20) for engaging one side of a bone rod (5) forming the end of a ligament (4). The body (15) comprises an axial hole having a tapered internal seat and being engaged by a screw. Slots (24) enable the body (15) to be expanded by the axial screw. When the body (15) is expanded (13, 14), the bone rod (5) is locked in place in a hole (7) formed in the bone (2). Reliable and easily performed and adjusted ligament anchoring may thus be achieved.

12 Claims, 5 Drawing Sheets

LIGAMENT ANCHORING DEVICE

TECHNICAL FIELD OF THE INVENTION

The present invention concerns means for attaching a ligament to a bone.

In orthopedic surgery it is frequently necessary to attach the end of a ligament to the bone of a patient, whether this is a ligament prosthesis comprising an artificial ligament or a living ligament taken from another part of the body of the patient.

Various anchoring techniques have been used until now. For example, document FR-A-2 696 925 describes an anchoring technique in which a hole is made in the bone tissue of the bone to which the ligament must be attached, a graft is taken consisting of a ligament central part attached to bone end parts in the form of a rod, one of the bone rods is inserted into the hole in the bone tissue and an axial screw is inserted in parallel into the same hole, beside the bone rod, applying force laterally both to the bone rod and to the wall of the bone tissue hole. The anchorage is effective but the surgeon cannot easily adjust the axial tension in the ligament during implantation and, more importantly, there is the risk of the ligament being weakened by the edges of the screw, which cut into it, in particular when the ligament end is to be anchored into a blind hole from the interior of the joint. Document EP-A-0 596 829 describes a similar anchorage with an oblique screw which additionally clamps the end of the ligament, which can also weaken the ligament.

In document FR-A-2 586 927 the end of the ligament is hollow and tubular and a conical plug is inserted into the hollow tube to press the wall of the tubular part of the ligament against a conical portion of a hole in the bone tissue. Clearly an anchorage of the above kind is not suitable for anchoring a living ligament, in which it is not easy to form a tubular end, and the surgeon will obviously find it very difficult to adjust the tension in the ligament during implantation.

In document EP-A-0 596 177 the end of the ligament is immobilized in a hole in the bone tissue by a transverse clamping screw. The screw can shear the end of the ligament and weaken the anchorage.

In document FR-A-2 671 717 a device is provided to anchor the end of the an artificial ligament prosthesis consisting of a wick or braid of a physiologically compatible woven material. The anchorage is provided by a pin having an expandable cylindrical shank partially inserted into a hole in the bone and receiving a screw in an axial bore in the shank to expand the shank radially and immobilize it in the hole. The prosthesis end fits around the part of the shank projecting out of the bone and is pressed against the external surface of the bone by the front face of a cylinder having a diameter greater than that of the shank and forming a head on the pin. The prosthesis is external to the bone and extends radially of the shank and of the hole in the bone. An anchorage of the above kind is not suitable for retaining a living ligament, which is weakened by the relatively large diameter hole needed in the ligament for the shank to pass through.

Document DE-U-92 10 031 concerns an expandable plug for anchorage in concrete. This is a technical field remote from that of the present invention. The plug has an expandable shank the outside surface of which has a square section to define longitudinal edges opposing rotation in the hole in the concrete. Expansion is effected in a diagonal direction by a central axial screw by virtue of four longitudinal slots perpendicular to the four side faces. Thus the side faces are not plane and are interrupted by the longitudinal slots. In the conventional manner, the object anchored by the plug remains outside the concrete.

SUMMARY OF THE INVENTION

The problem addressed by the present invention is that of designing a new ligament anchoring device that assures an effective and reliable anchorage without risk of shearing the ligament and which makes it very easy for the surgeon to adjust the tension in the ligament during implantation without requiring any additional prestressing of the ligament.

Another object of the invention is to design an anchoring device of the above type which, once fitted, does not have any part projecting externally of the bone.

To achieve the above and other objects, a ligament anchoring device in accordance with the invention, for fixing the end of a ligament to a bone, comprises:

an elongate body along a longitudinal axis and delimited by a peripheral side surface, a proximal end and a distal end, a longitudinal axial hole in the body open at its proximal end at least, at least one interior constriction of the axial hole, longitudinal slots through the body and distributed around the perimeter of its peripheral surface at least in the vicinity of the area occupied by the constriction of the axial hole, an axial core housed in the axial hole in the body and movable longitudinally to bear against the constriction of the axial hole on a contact surface adapted to expand the body by this means, and means accessible from the proximal end of the body for selectively moving the axial core in the longitudinal direction, anti-rotation projections are formed on the external surface of the body to prevent it rotating in the hole in the bone tissue, a generally flat lateral bearing face forms a part of the peripheral side surface of the body and is adapted to bear against a side of the end of the ligament inserted side by side with the body in a hole in the bone tissue opening onto the exterior surface of the bone, the peripheral side surface of the body has a generally constant cross-section throughout its length.

In a first embodiment:

the axial hole has an internally screwthreaded rigid portion with no longitudinal slots, the axial core and the means for moving it axially comprise a screw the shank of which has a screwthreaded portion functionally inserted in the screwthreaded portion of the axial hole, the screw having a portion adapted to bear, during screwing, against a conical constriction of the axial hole and thereby expand the body.

In a first variant of the first embodiment the larger diameter screw portion is formed by the distal screw end opposite the screw head. In this case, the screw head preferably has a polygonal cross-section with rounded corners forcibly inserted at the end of screwing into a proximal end portion of the body with longitudinal slots through it and having a diameter less than that of the screw head.

In a second variant of the first embodiment the larger diameter screw portion is formed by the proximal screw head inserted in a proximal conical portion of the axial body hole.

In a second embodiment:

the axial core slides freely and longitudinally in the axial hole and is coupled to the body by means for preventing axial rotation, the axial core has a screwthreaded axial bore, a screw with a screwthreaded shank and a proximal head is inserted in the axial hole in the body with its head in axial bearing engagement against the proximal end of the body and with its shank functionally inserted in the screwthreaded axial bore of the axial core so that rotation of the screw moves the axial core axially and expands the body.

In a first variant of the second embodiment the screw head has a conical bearing face engaged against a second conical portion of the axial hole associated with second longitudinal slots constituting a second expandable portion of the body.

The conical portions can have a circular cross-section, constituting a circular conical portion, or can have a polygonal cross-section, constituting a pyramidal portion.

BRIEF DESCRIPTION OF THE DRAWINGS

Other objects, features and advantages of the present invention will emerge from the following description of particular embodiments given with reference to the accompanying drawings, in which.

DESCRIPTION OF THE PREFERRED EMBODIMENTS

Figure 1:
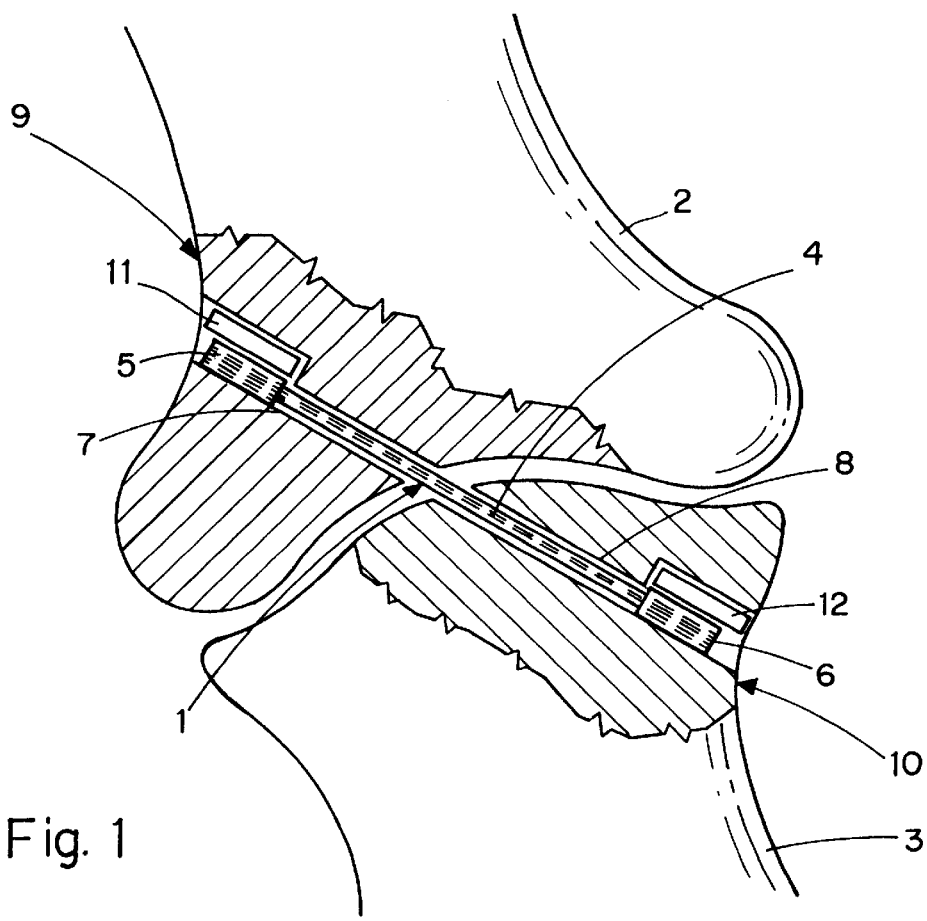
FIG. 1 is a part-sectional schematic side view of a ligament prosthesis linking two bone ends and anchored by two ligament anchoring devices in accordance with the present invention.

In the example shown in FIG. 1 a ligament prosthesis 1 is adapted to connect a first bone 2 to a second bone 3. The ligament prosthesis 1 comprises a central ligament 4 attached at its first end to a first bone rod 5 and attached at its second end to a second bone rod 6. The ligament prosthesis 1 is inserted in two holes 7 and 8 respectively formed in the first bone 2 and in the second bone 3. Near the external surface 9 or 10 of the corresponding bone 2 or 3 the respective hole 7 or 8 has an enlarged section enabling insertion of an anchoring device 11 or 12 in accordance with the invention parallel to the axis of the hole 7 or 8 and alongside the corresponding bone rod 5 or 6.

Figure 2:
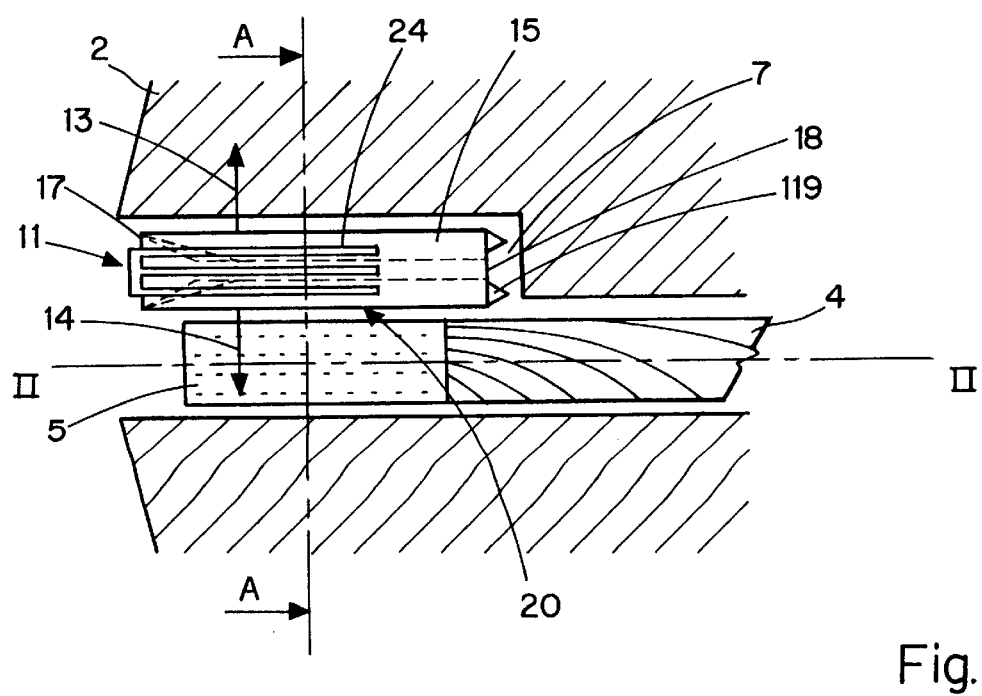
FIG. 2 is a sectional side view to a larger scale of one of the two ligament anchoring devices from FIG. 1.

As can be seen more clearly in FIG. 2, the hole 7 formed in the bone tissue of the bone 2 and extending longitudinally along the axis II—II receives a portion of the ligament 4, the bone rod 5 that terminates the ligament 4 and the anchoring device 11. The bone rod 5 is elongate and the anchoring device 11 is also elongate. They are disposed side by side in the hole 7, parallel to the axis II—II of the hole. The anchoring device 11 is a selectively expandable element in the radial direction as shown by the arrows 13 and 14 for wedging the bone rod 5 into the bone 2. The anchoring device 11 is preferably expanded progressively so as to enable the surgeon to adjust the position of the bone rod 5 in the hole 7 easily and accurately in order to adjust the tension in the ligament 4 during implantation. The expansion of the anchoring device 11 is preferably reversible, enabling the surgeon to reduce the expansion to release the bone rod 5 temporarily if further adjustment of the tension in the ligament is necessary.

In all the embodiments shown hereinafter the anchoring device 11 comprises an elongate body 15 extending along a longitudinal axis I—I and delimited by a peripheral side surface 16, a proximal end 17 and a distal end 18.

Figure 3:
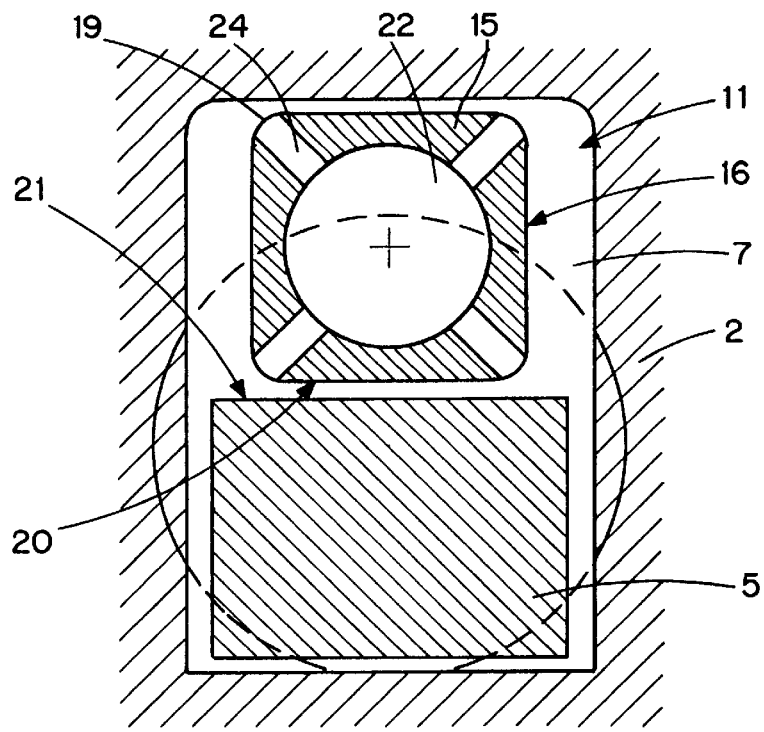
FIG. 3 is a schematic view in cross-section taken along the line A—A in FIG. 2.

Anti-rotation projections are formed on the external surface of the body 15, for example on the peripheral side surface 16 of the body 15, to prevent it rotating in the hole 7 in the bone tissue. In particular, as shown in FIG. 3, the body 15 can have a substantially constant polygonal section throughout its length, for example a square section, thus having edges like the edge 19 constituting an anti-rotation projection preventing the body 15 rotating in the hole 7 in the bone tissue. Alternatively, as shown in FIG. 2, front projections 119 can be provided on the distal front face 18 of the body 15.

Part of the peripheral side surface 16 of the body 15 is generally plane and continuous to form a generally flat side bearing face 20. This side bearing face 20 is adapted to bear against a side 21 of the bone rod 5 forming the end of the ligament 4.

Figure 4:
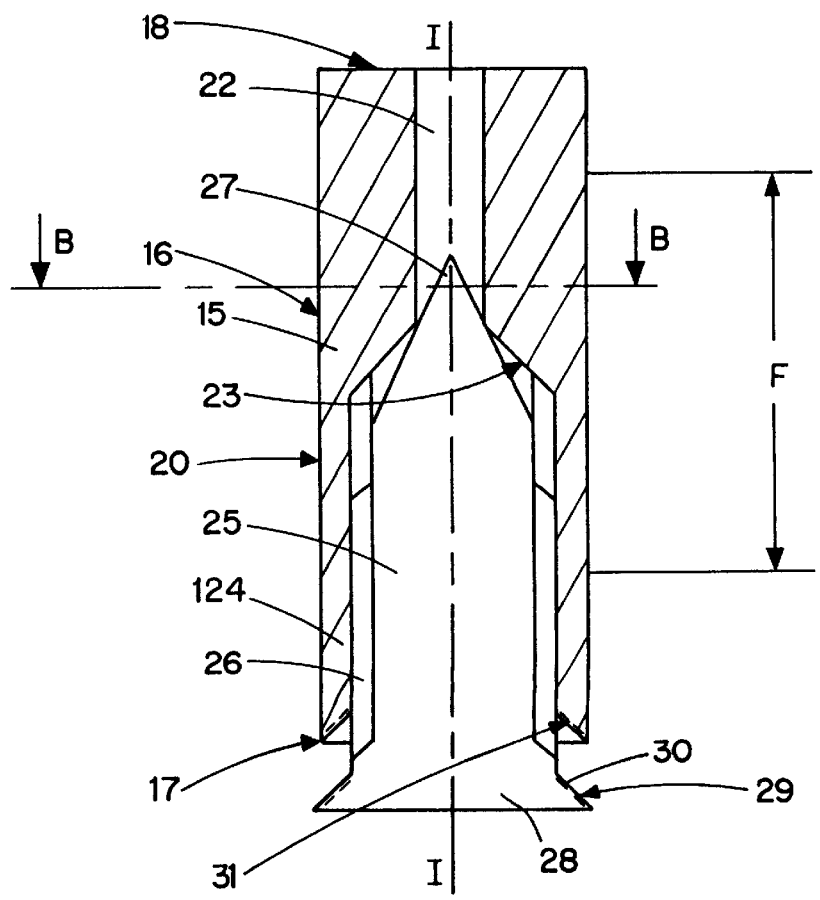
FIG. 4 is a side view in longitudinal section of a first embodiment of a ligament anchoring device of the present invention.
Figure 5:
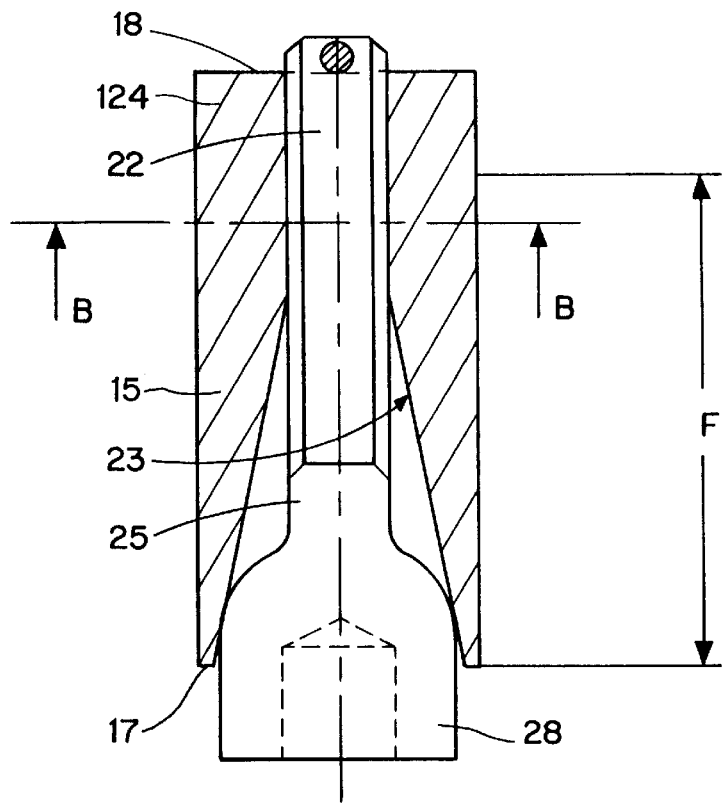
FIG. 5 is a side view in longitudinal section of a variant of the FIG. 4 embodiment of a ligament anchoring device.

A longitudinal axial hole 22 is formed in the body 15 and is open at least at its proximal end 17. The axial hole 22 has at least one conical portion 23. Longitudinal through slots, like the slot 24, are distributed around the perimeter of the peripheral surface 16 of the body 15 near the area occupied by the conical portion 23 of the axial hole 22. In FIG. 4, for example, slots like the through slot 24 (FIGS. 2 and 3) are distributed over a length F on either side of the conical portion 23. In FIGS. 2 and 5 the slots, like the slot 24, are disposed from the proximal end 17 over approximately two-thirds of the length of the body 15 towards the distal end 18, the conical portion 23 occupying substantially the same length F. FIG. 3 shows an embodiment with four slots 24 in cross-section taken along the line B—B in FIGS. 4 through 8. It can be seen that the slots 24 are advantageously disposed diagonally to connect the apexes of the square section with the result that the lateral bearing face 20 is continuous, i.e. free of slots.

In all the embodiments an axial core is accommodated in the axial hole 22 in the body 15 and can be moved longitudinally to bear against the conical portion 23 of the axial hole 22 and thereby expand the body 15. Means accessible from the proximal end 17 of the body 15 move the axial core selectively in the longitudinal direction to expand or contract the body 15.

In the FIG. 4 embodiment the axial hole 22 has an internally screwthreaded rigid portion 124 with no longitudinal slots. The axial core and the means for moving it axially are then in the form of a screw 25 the shank of which has a screwthreaded portion 26 functionally inserted in the screwthreaded rigid proximal portion 124 of the body 15 with the axial hole 22, the distal end 27 of the screw 25 opposite the screw head 28 having a conical portion inserted in the conical portion 23 of the axial hole 22 to expand the slotted intermediate part F of the body 15 when the screwthreaded portion 26 of the screw 25 is screwed into the screwthreaded portion 124 of the body 15.

The screw 25 can have a head 28 with means for engaging a screwdriving tool, for example a polygonal section blind axial hole.

In the embodiment shown in FIG. 4 the screw head 28 has a conical bearing face 29 with radial striations 30 engaging at the end of screwing against a corresponding striated conical proximal face 31 of the body 15 to oppose unscrewing of the screw 25.

Alternatively, the proximal end 17 of the body 15 and the screw head 28 can be slotted to render them flexible to produce a reversible clipping engagement opposing unintentional unscrewing of the screw.

In the variant shown in FIG. 5 the conical portion 23 of the axial hole 22 is the hole portion nearest the proximal end 17 of the body 15 and the rigid portion 124 of the body 15 is near the distal end 18. The proximal head 28 with the flared bearing face of the screw 25 bears against the proximal conical portion 23 of the axial hole 22 in the body 15. The slots extend along the proximal portion F of the body 15.

Figure 6:
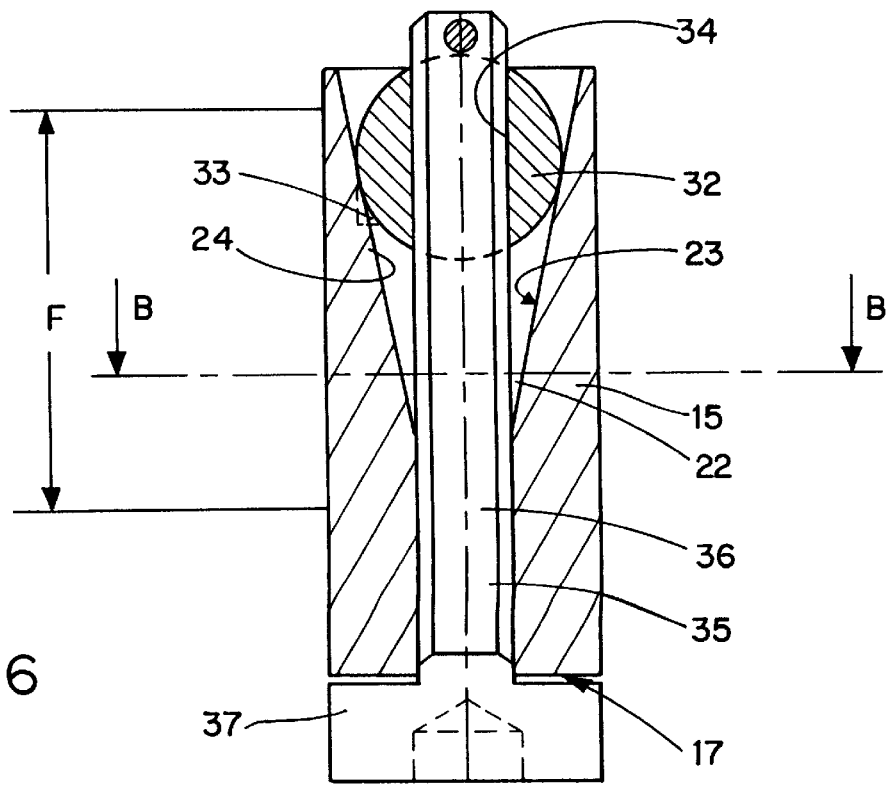
FIG. 6 is a side view in longitudinal section of a second embodiment of a ligament anchoring device of the present invention.

In the FIG. 6 embodiment an axial core 32 slides freely in the longitudinal direction in the axial hole 22 and is coupled to the body 15 by means for preventing axial rotation. For example, the axial core 32 has on its peripheral surface a radial immobilizing lug 33 engaged in one of the slots 24 in the body 15 to prevent it rotating. The axial core 32 has a screwthreaded axial bore 34. A screw 35 with a screwthreaded shank 36 and a proximal head 37 is inserted in the axial hole 22 in the body 15. The head 37 bears axially against the proximal end 17 of the body 15. The screw shank 36 is functionally inserted in the screwthreaded axial hole 34 in the axial core 32. Rotating the screw 35 moves the axial core 32 axially and expands the body 15 because the axial core 32 is in bearing engagement inside the conical part 23 of the axial hole 22 in the body 15. The slots like the slot 24 are in the distal part F of the body 15 including the conical part 23 of the axial hole 22. In the FIG. 6 embodiment the screw head 37 has a shoulder and bears against a front face of the proximal end 17 of the body 15.

Figure 7:
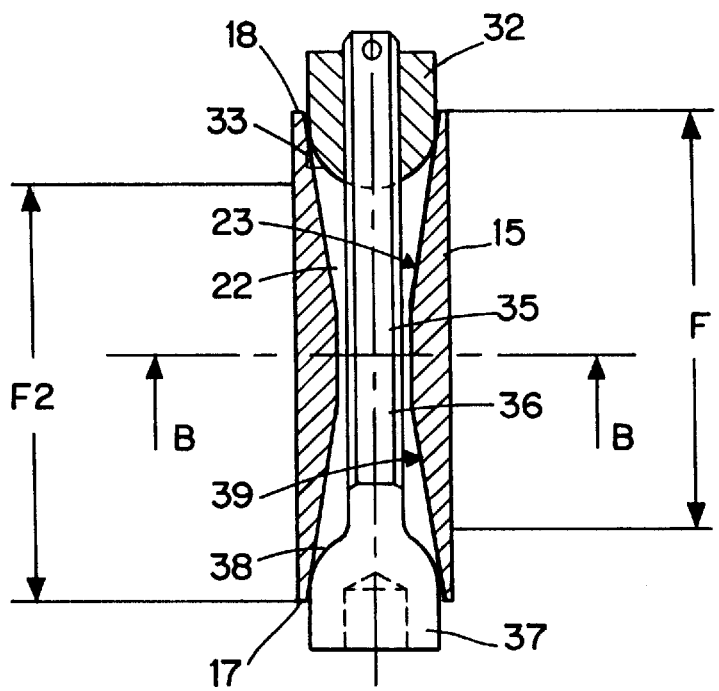
FIG. 7 is a side view in longitudinal section of a variant of the FIG. 6 embodiment of a ligament anchoring device.

The variant shown in FIG. 7 includes the same means as the FIG. 6 embodiment and corresponding parts are identified by the same reference numbers.

In the FIG. 7 variant the difference is that the screw head 37 has a conical or flared bearing face 38 engaged against a second conical portion 39 of the axial hole 22 associated with second longitudinal slots F2 constituting a second expandable portion of the body 15. The body 15 therefore has a first expandable portion F near the distal end 18 and a second expandable portion F2 near the proximal end 17.

Figure 8:
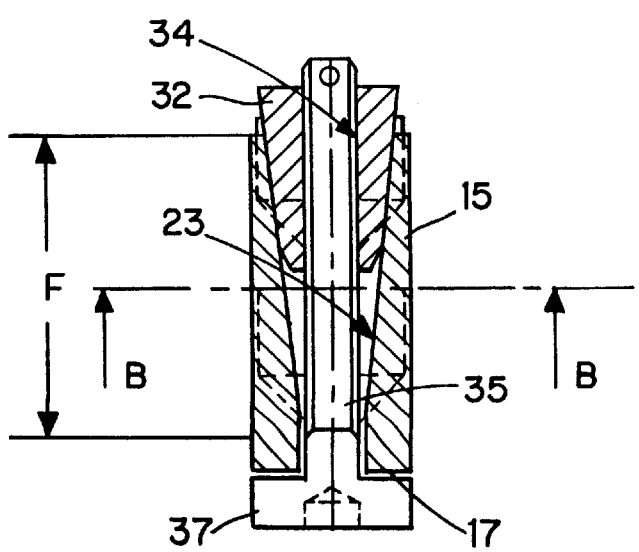
FIG. 8 is a side view in longitudinal section of another variant of the FIG. 6 embodiment of a ligament anchoring device.

FIG. 8 shows a variant of the FIG. 6 embodiment in which corresponding parts are identified by the same reference numbers. The modification is in the particular shape of the axial core 32 which is generally spherical in the FIG. 6 embodiment and generally frustoconical in the FIG. 8 variant.

In all the embodiments shown the peripheral side surface 16 of the body 15 advantageously has anti-slip projections opposing axial sliding of the body 15 in the hole 7 in the bone tissue and simultaneously opposing relative axial slipping between the body 15 and the bone rod 5 to be immobilized and forming the end of the ligament 4.

Figure 10:
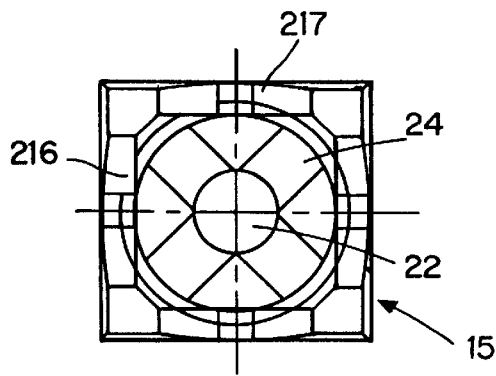
FIG. 10 is an end view of the anchor body from FIG. 9.
Figure 9:
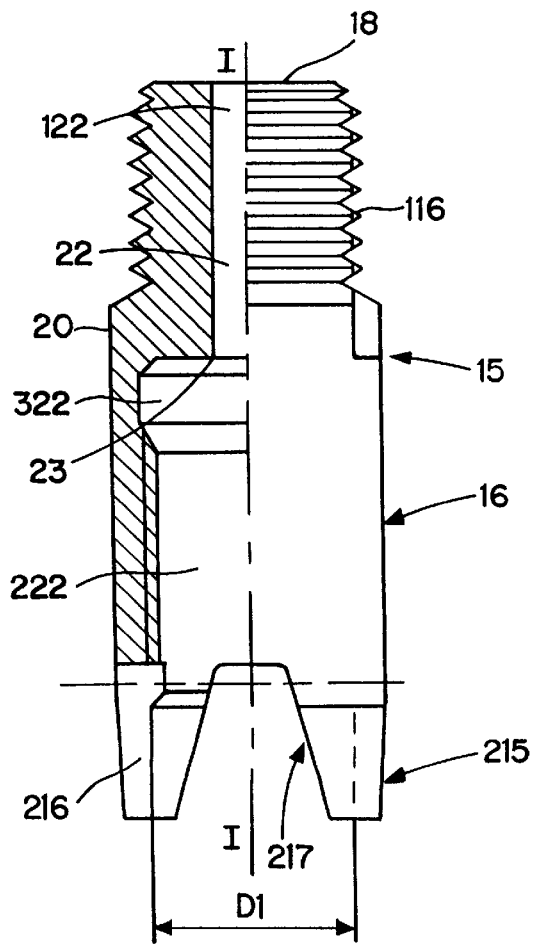
FIG. 9 is a side view in longitudinal half-section of an anchor body in another variant of the first embodiment of the present invention.
Figure 11:
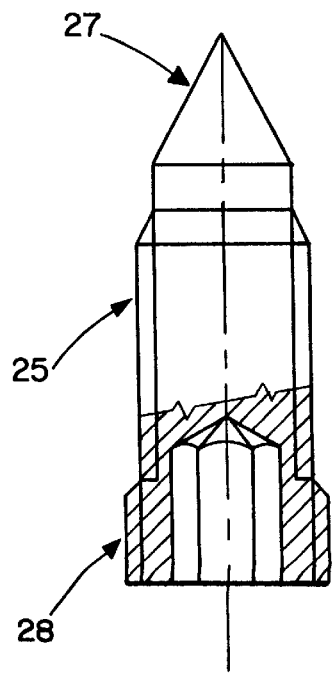
FIG. 11 is a part-sectional side view of an expansion screw that fits the anchor body from FIG. 9.

The embodiment shown in FIGS. 9 through 11 relates to the embodiment shown in FIGS. 3 and 4. To avoid the necessity to repeat the description corresponding parts of the two embodiments are identified by the same reference numbers.

They include the elongate anchor body 15 along the longitudinal axis I—I with its peripheral side surface 16 having a generally flat side bearing face 20, an axial hole 22 with a constriction 23 between a relatively narrower distal hole portion 122 and a relatively wider proximal hole portion 222, and four slots 24. The distal portion 122 of the hole 22 is formed by the crossing over of the four diagonal slots 24, as can be seen more clearly in FIG. 10. The diagonal slots 24 extend over the length of the anchor body 15 occupied by the distal portion 122 of the hole 22 between the distal end 18 and the constriction 23.

At the proximal end the constriction 23 is flanked by a larger diameter area 322 of the axial hole 22 favoring radial elastic deformation of the body 15 in the area of the constriction 23. As can be seen in FIG. 10, the exterior surface 16 of the anchor body 15 is generally parallelepiped shape with a square section and anti-slip projections 116 in the distal portion in the form of triangular section circular ribs.

The anchor body 15 has a proximal end portion 215 with longitudinal slots through it like the slots 216 and 217 and the inside diameter D1 of which optionally varies to form a slight conicity with the apex at the distal end.

Figure 12:
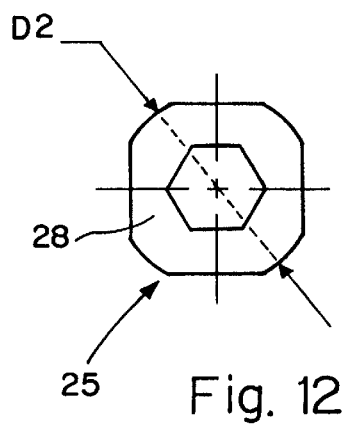
FIG. 12 is an end view of the screw head from FIG. 11.

In this embodiment the axial core is also a generally cylindrical body screw 25 with a conical distal end 27 with a cone angle of approximately 60° adapted to be inserted into the constriction 23 in the anchor body 15. The proximal end of the screw 25 is a head 28 with a polygonal cross-section with rounded corners, for example a square section as shown in FIG. 12, forcibly inserted at the end of screwing into the proximal end portion 215 of the anchor body 15. The diameter D2 of the two diagonals of the screw head 28 is greater than the diameter D1 of the interior passage in the proximal end portion 215 of the body. Elastic deformation of the proximal end portion 215 with longitudinal slots 216 and 217 through it prevents rotation of the screw 25 at the end of screwing.

Accordingly, a ligament prosthesis in accordance with the invention comprises an anchoring device 11 inserted side by side into a hole 7 in the bone tissue with a bone rod 5 forming the end of a ligament 4.

The anchoring device of the invention is made from biocompatible materials, possibly bioresorbable materials. The anchor body 15 can be made of polyethylene, for example, and the expansion screw 25 can be made of stainless steel, titanium or polyethylene.

The present invention is not limited to the embodiment explicitly described but encompasses variants and generalizations thereof within the scope of the following claims.

I claim:

1. A ligament anchoring device for fixing the end (5) of a ligament (4) to a bone (2), comprising:

an elongate body (15) along a longitudinal axis (I—I) and delimited by a peripheral side surface (16), a proximal end (17) and a distal end (18), a longitudinal axial hole (22) in the body (15) open at its proximal end (17) at least, at least one interior constriction (23) of the axial hole (22), longitudinal slots (24) through the body (15) and distributed around the perimeter of its peripheral surface (16) at least in the vicinity of the area occupied by the constriction (23) of the axial hole (22), an axial core (25, 32) housed in the axial hole (22) in the body (15) and movable longitudinally to bear against the constriction (23) of the axial hole (22) on a contact surface adapted to expand the body (15) by this means, means (25, 35) accessible from the proximal end (17) of the body (15) for selectively moving the axial core (25, 32) in the longitudinal direction (I—I), wherein:

anti-rotation projections (19) are formed on the external surface (16) of the body (15) to prevent it rotating in the hole (7) in the bone tissue, a generally flat lateral bearing face (20) forms a part of the peripheral side surface (16) of the body (15) and is adapted to bear against a side (21) of the end (5) of the ligament (4) inserted side by side with the body (15) in a hole (7) in the bone tissue opening onto the exterior surface (9) of the bone (2).

2. An anchoring device according to claim 1 wherein:

the axial hole (22) has an internally screwthreaded rigid portion (124) with no longitudinal slots (24), the axial core and the means for moving it axially comprise a screw (25), the screw having a shank, the shank having a screwthreaded portion functionally inserted in the screwthreaded portion (124) of the axial hole (22), the screw (25) having a portion (27, 38) adapted to bear, during screwing, against a conical constriction (23) of the axial hole (22) and thereby expand the body (15).

3. An anchoring device according to claim 1 wherein:

the axial hole (22) has an internally screwthreaded rigid portion (124) with no longitudinal slots (24), the axial core and the means for moving it axially comprise a screw (25), the screw having a shank, the shank having a screwthreaded portion functionally inserted in the screwthreaded portion (124) of the body (15) with the axial hole (22), the screw (25) having a conical portion (27) adapted to bear, during screwing, against the constriction (23) of the axial hole (22) and thereby expand the body (15).

4. An anchoring device according to claim 3 wherein the screw portion (25) adapted to bear against the constriction (23) of the axial hole (22) is formed by the distal end (27) of the screw (25) opposite the screw head (28).

5. An anchoring device according to claim 4 wherein the screw head (28) has a polygonal cross-section with rounded corners forcibly inserted at the end of screwing into a proximal end portion (215) of the body (15) having longitudinal slots (216, 217) through it and a diameter less than that of the screw head (28).

6. An anchoring device according to claim 2 wherein the screw portion (25) adapted to bear against the conical portion (23) of the axial hole (22) is formed by the proximal screw head (28) inserted in a corresponding proximal conical portion (23) of the axial hole (22) in the body (15).

7. An anchoring device according to claim 1 wherein:

the axial core (32) slides freely and longitudinally in the axial hole (22) and is coupled to the body (15) by means (33) for preventing axial rotation, the axial core (32) has a screwthreaded axial bore (34), a screw (35) with a screwthreaded shank (36) and a proximal head (37) is inserted in the axial hole (22) in the body (15) with its head (37) in axial bearing engagement against the proximal end (17) of the body (15) and with its shank (36) functionally inserted in the screwthreaded axial bore (34) of the axial core (32) so that rotation of the screw (35) moves the axial core (32) axially and expands the body (15).

8. An anchoring device according to claim 7 wherein the screw head (37) has a conical bearing face (38) engaged against a second conical portion (39) of the axial hole (22) associated with second longitudinal slots (F2) constituting a second expandable portion of the body (15).

9. An anchoring device according to claim 7 wherein the axial core (32) has on its peripheral surface a radial immobilizing lug (33) inserted in one of the slots (24) of the body (15) to prevent it rotating.

10. An anchoring device according to claim 1 wherein the peripheral side surface (16) of the body (15) has anti-slip projections opposing axial sliding of the body (15) in the hole (7) in the bone tissue and opposing relative axial sliding between the body (15) and the end (5) of the ligament (4).

11. A ligament prosthesis comprising an anchoring device according to claim 1 inserted side by side in a hole (7) in the bone tissue with a bone rod (5) forming the end of a ligament (4).

12. A ligament anchoring device for fixing an end of a ligament to a bone, comprising:

an elongate body, delimited by a peripheral side surface, a proximal end, and a distal end, a longitudinal axial hole in the body, the axial hole being open at least at said proximal end, at least one interior constriction of the axial hole, longitudinal slots through the body and distributed around a perimeter of its peripheral surface at least in a vicinity of an area occupied by the constriction of the axial hole, an axial core housed in the axial hole in the body and movable longitudinally to bear against the constriction of the axial hole on a contact surface adapted to expand the body in response to movement of the axial core, and means, accessible from the proximal end of the body, for selectively moving the axial core in a longitudinal direction, wherein a generally flat lateral bearing face forms a part of the peripheral side surface of the body and is adapted to bear against a side of the end of the ligament inserted side by side with the body in a hole in bone tissue opening onto an exterior surface of a bone, and wherein the peripheral side surface of the body has a generally constant cross-section throughout its length.

\* \* \* \* \*